United States Patent [19]
Restive

[11] Patent Number: 5,881,493
[45] Date of Patent: Mar. 16, 1999

[54] METHODS FOR APPLYING FOAM

[75] Inventor: Mario John Restive, Frankfort, N.Y.

[73] Assignee: D. B. Smith & Co. Inc., New York Mills, N.Y.

[21] Appl. No.: 528,080

[22] Filed: Sep. 14, 1995

[51] Int. Cl.[6] ................................................ A01M 7/00
[52] U.S. Cl. ............................................ 43/124; 43/132.1
[58] Field of Search .................................. 239/8, 10, 373, 239/355, 360, 364, 365, 366, 368, 370, 343, 526, 532, 372; 43/132.1, 124

[56] References Cited

U.S. PATENT DOCUMENTS

| | | |
|---|---|---|
| 666,072 | 1/1901 | Sherman . |
| 1,290,544 | 1/1919 | Graumann . |
| 1,401,386 | 12/1921 | Woodberry . |
| 1,457,895 | 6/1923 | Campenella ............................ 239/343 |
| 1,786,889 | 6/1930 | Brandt ..................................... 237/355 |
| 2,090,727 | 8/1937 | Gosmann .................................. 261/94 |
| 2,514,107 | 7/1950 | Trostler ..................................... 299/89 |
| 2,532,565 | 12/1950 | Miller ......................................... 259/4 |
| 2,651,546 | 9/1953 | Palm ....................................... 299/107 |
| 2,653,848 | 9/1953 | Lee ........................................... 299/83 |
| 2,780,025 | 2/1957 | Finnigan .................................... 43/124 |
| 2,916,855 | 12/1959 | Thiegs ......................................... 47/58 |
| 2,965,309 | 12/1960 | Parrot ....................................... 239/343 |
| 3,123,254 | 3/1964 | Rabby et al. . |
| 3,209,554 | 10/1965 | MacManus ............................... 62/306 |
| 3,388,868 | 6/1968 | Watson et al. ........................... 239/427 |
| 3,524,911 | 4/1968 | Leavitt ....................................... 424/45 |
| 3,589,054 | 6/1971 | Pascucci .................................... 43/124 |
| 3,618,856 | 11/1971 | Sachnik ....................................... 239/8 |
| 3,767,078 | 10/1973 | Gortz et al. . |
| 3,791,778 | 2/1974 | Eron ........................................ 418/15 |
| 3,816,610 | 6/1974 | Lusby ........................................ 424/17 |
| 3,836,076 | 9/1974 | Conrad et al. .............................. 239/8 |
| 4,042,217 | 8/1977 | Snider et al. ................................ 259/4 |
| 4,071,195 | 1/1978 | Kuhns et al. ............................. 239/289 |
| 4,318,443 | 3/1982 | Cummins ................................. 239/366 |
| 4,324,350 | 4/1982 | Thompson . |

(List continued on next page.)

FOREIGN PATENT DOCUMENTS

| | | | |
|---|---|---|---|
| 268733 | 12/1965 | Australia ............................... 239/343 |
| 39918 | 3/1932 | France ................................... 239/355 |

OTHER PUBLICATIONS

Kalo, PCO Foam, Foam Concentrate.
Kalo, Kalo Fills You In On Foam.
The Fountainhead Group, Inc., Professional Applicators Catalog, Jan. 1995.
B & G Equipments Company, Trouble–Shooter Portable Foaming and Liquid Borate Unit.
Johnson & Son, Inc., Raid Home Barrier Insecticide.

*Primary Examiner*—Kevin Weldon
*Attorney, Agent, or Firm*—Bond, Schoeneck & King LLP

[57] ABSTRACT

A foam sprayer apparatus comprises a container and a manual air pump carried by the container. The pump is operable to manually pump air into the container and create an air head therein. A discharge channel establishes fluid communication between the interior and exterior of the container. The channel contains an air opening located inside the tank and above a level to which a supply of foaming composition is to be filled. An inlet of the discharge channel is located below the level to which a supply of foaming composition is to be filled. A foaming chamber is also included for causing turbulence in a fluid received from the discharge channel. A discharge valve controls the flow of fluid through the discharge channel and foaming chamber. When the valve is open, fluid flows from the discharge channel to the foaming chamber, and from the foaming chamber to a nozzle. The nozzle is in fluid communication with the outlet of the foaming chamber. The nozzle is normally coupled to a spray wand which is placed between the discharge valve and nozzle. The nozzle functions to discharge, under pressure, foam received from the foaming chamber when the discharge valve is opened. Methods of applying foam are also contemplated. One such method concerns the treatment of insects using an insecticidal foaming composition and a manual compressed-air sprayer which has been modified in accordance with the present invention.

5 Claims, 5 Drawing Sheets

U.S. PATENT DOCUMENTS

| | | | |
|---|---|---|---|
| 4,423,829 | 1/1984 | Katz . | |
| 4,624,070 | 11/1986 | Query et al. | 43/132.1 |
| 4,651,468 | 3/1987 | Martinez et al. | 47/80 |
| 4,655,394 | 4/1987 | Ferrazza et al. | 239/412 |
| 4,688,349 | 8/1987 | Renth | 43/132.1 |
| 4,822,613 | 4/1989 | Rodero | 424/405 |
| 4,836,939 | 6/1989 | Hendrickson | 252/3 |
| 4,867,208 | 9/1989 | Fitzgerald et al. . | |
| 4,875,508 | 10/1989 | Burke, II et al. . | |
| 4,889,710 | 12/1989 | Hagarty | 424/45 |
| 4,901,925 | 2/1990 | Blake, III | 239/343 |
| 4,917,299 | 4/1990 | Kondo et al. | 239/8 |
| 4,975,425 | 12/1990 | Barnett, Jr. | 514/119 |
| 4,997,592 | 3/1991 | Woogerd | 252/354 |
| 5,094,853 | 3/1992 | Hagarty | 424/405 |
| 5,104,658 | 4/1992 | Hagarty | 424/405 |
| 5,111,971 | 5/1992 | Winer . | |
| 5,116,618 | 5/1992 | Hagarty | 424/405 |
| 5,187,498 | 2/1993 | Burger . | |
| 5,222,633 | 6/1993 | Blake | 222/179 |
| 5,303,853 | 4/1994 | Nye . | |
| 5,319,878 | 6/1994 | Moffett et al. | 43/124 |
| 5,346,699 | 9/1994 | Tiernan et al. | 424/405 |
| 5,368,231 | 11/1994 | Brunerie et al. | 239/145 |
| 5,394,643 | 3/1995 | Schmittmann | 43/124 |
| 5,411,177 | 5/1995 | Blake, III | 222/105 |

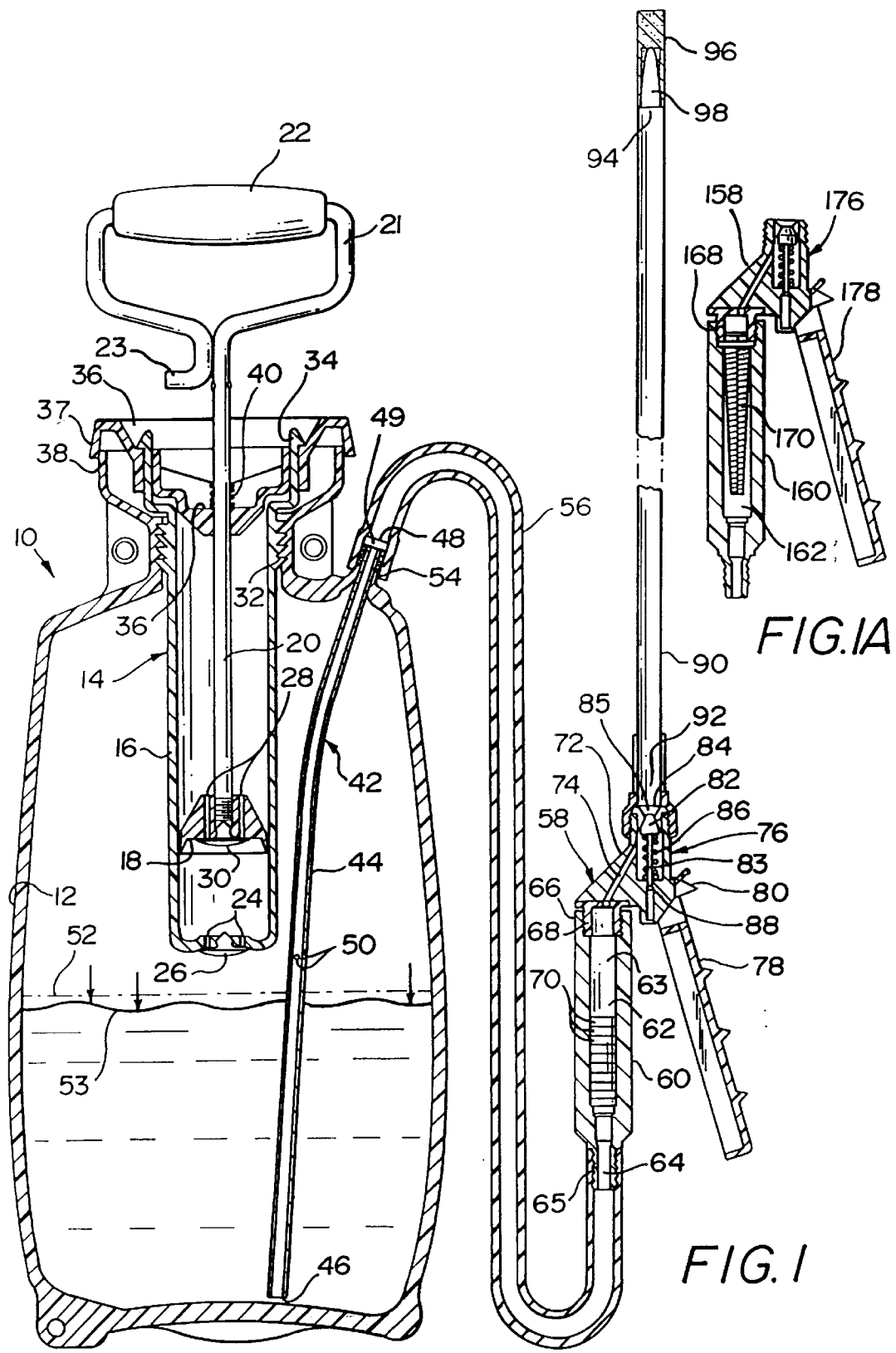

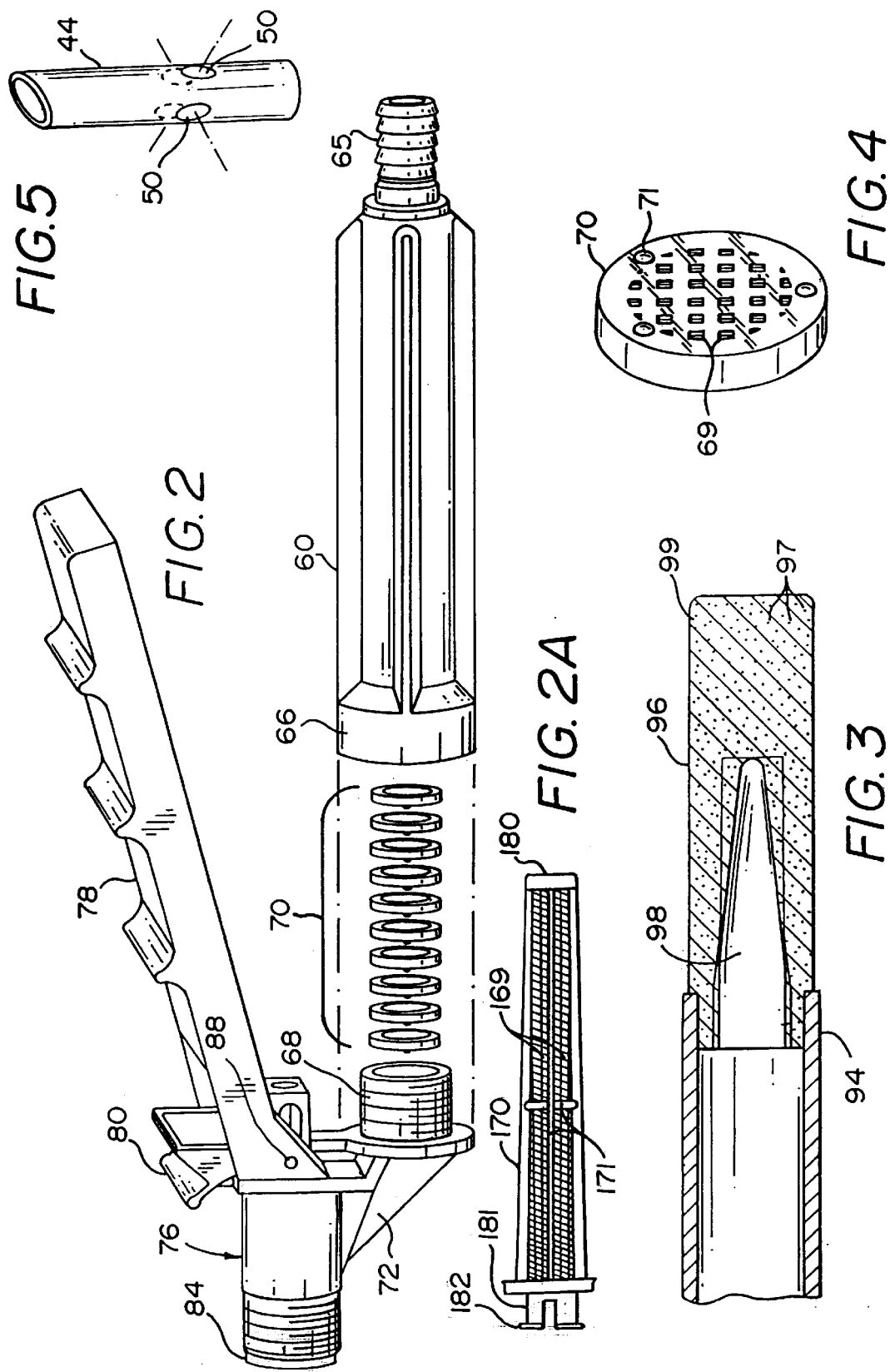

METHODS FOR APPLYING FOAM

BACKGROUND OF THE INVENTION

1. Technical Field

The present invention relates generally to foam generating apparatus and methods of applying foam produced by said apparatus, including the application of insecticidal foams for the treatment of insects. The present invention also has a particular application in the field of treating fire ants.

2. Background Art

There are numerous apparatus available for generating foams for various applications. Such applications include, for example, cleaning, fire extinguishing, chemical containment, and insect treating. Many of these apparatus require electric or gasoline power sources for operating compressors and pumps to produce and deliver the foam. As a result, these apparatus must carry batteries, electrical cords, internal combustion engines, and the like. Examples of such devices are described in U.S. Pat. No. 5,319,878 to Moffett et al.; U.S. Pat. No. 5,346,699 to Tiernan et al.; U.S. Pat. No. 4,688,349 to Renth; U.S. Pat. No. 3,618,856 to Sachnik; U.S. Pat. No. 3,589,054 to Pascucci; and a product brochure published by B&G Equipment Company, Plumsteadville, Pa., entitled, Trouble-Shooter Portable Foaming and Liquid Borate Unit. Such apparatus are expensive, cumbersome, and they usually require training to operate and specialized maintenance.

Inexpensive and easy to operate apparatus, employing manual pumps, have been used to produce foam for cleaning applications. For example, U.S. Pat. No. 5,222,633 to Blake, U.S. Pat. No. 2,653,848 to Lee, and a product catalog by The Fountainhead Group, Inc., New York Mills, N.Y., entitled, Professional Applicators Catalog ("Convenience Applicator"), all describe such foaming devices. However, the utility of these devices are limited to cleaning applications. Such devices are not suitable for producing and delivering foams for other applications, such as the treatment of insects.

The application of insecticidal foams for the treatment and control of insects has been known for a number of years. For example, U.S. Pat. No. 4,822,613 to Rodero describes an insecticidally-active foam for producing a positive insect barrier in a cavity. U.S. Pat. No. 5,346,699 to Tiernan et al. describes an insecticidal foam for treating termites under concrete slabs or around concrete foundations. Other insecticidal foams are described in U.S. Pat. No. 5,116,618 to Hagarty, U.S. Pat. No. 5,104,658 to Hagarty, U.S. Pat. No. 5,094,853 to Hagarty, U.S. Pat. No. 4,975,425 to Barnett, Jr., U.S. Pat. No. 4,889,710 to Hagarty, and U.S. Pat. No. 3,524,911 to Leavitt. The apparatus suggested for the application of these foams are aerosol cans, spray pumps like those used for household cleaners, spray guns, and electric or gasoline powered pumps. As mentioned previously, the electric or gasoline powered apparatus are expensive, cumbersome, and usually require training and specialized maintenance. Aerosol cans and household spray pumps suffer from the drawback that they do not hold a large capacity of foam composition. In addition, household spray pumps would require constant trigger pumping for most insect treating applications. Finally, spray guns do not suggest any advantages over such apparatus. None of these insecticidal foam patents suggests a suitable apparatus for treating ants inside the ant mound.

The injection of liquid insecticides (rather than foam) into ant mounds has been accomplished by using apparatus as described in U.S. Pat. No. 4,624,070 to Query et al. and U.S. Pat. No. 1,290,544 to Graumann. This method of treating ants is much less efficient than employed by the present invention because liquid insecticide is absorbed by the soil and is thus drawn away from the tunnels and chambers inside the mound. Penetration of the insecticide is also limited because of absorption. As a result, much more liquid insecticide is needed to treat an ant mound than if an insecticidal foam is employed. This leads to waste and an increased threat to the environment. Moreover, the apparatus proposed in U.S. Pat. No. 4,624,070 to Query et al. and U.S. Pat. No. 1,290,544 to Graumann are not very portable or convenient to operate.

Another aspect of the present invention pertains to applying an insecticidal barrier around a structure, such as dwelling. Conventional methods of producing such a barrier involve spraying liquid insecticides along the target area. Liquid spraying can be inefficient when laying down a barrier, because some of the sprayed contents may be blown away before reaching the ground or other target area. In addition, a sprayed liquid barrier is virtually invisible, and thus makes it difficult for the operator to determine whether the barrier has been properly laid down. An insecticidal foam has been proposed to avoid some of these drawbacks in U.S. Pat. No. 4,997,592 to Woogerd. However, this patent does not suggest the use of foaming apparatus that avoid the problems and drawbacks hereinabove mentioned.

SUMMARY OF THE INVENTION

It is therefore an object of the present invention to provide foam spray apparatus and methods of foam application that avoid the problems associated with the prior art.

It is another object of the present invention to provide foam spray apparatus that are portable, easy to operate and require little maintenance.

It is a further object of the present invention to provide foam spray apparatus that will produce a high quality foam with good flow characteristics and life span.

It is yet another object of the present invention to provide foam spray apparatus that will produce a dense foam with a minimal decrease in head pressure, thus maximizing the pressure and flow rate of the foam.

It is yet a further object of the present invention to provide foam spray apparatus that are inexpensive to manufacture and maintain.

It is still another object of the present invention to provide foam spray apparatus that are suitable for a broad range of foaming applications.

It is still a further object of the present invention to provide foam spray apparatus that are suitable for the treatment of insects.

It is still yet another object of the present invention to provide foam spray apparatus and methods of foam application that result in the efficient application of insecticide to a target area, and thus reduce waste and the threat to the environment.

It is still yet a further object of the present invention to provide foam spray apparatus and methods of foam application that involve manual compressed-air sprayers for the production and application of insecticidal foam.

It is still yet a further object of the present invention to provide foam spray apparatus and methods for treating fire ants in a fire ant mound.

It is still yet a further object of the present invention to provide foam spray apparatus and methods for applying an insecticidal barrier around a structure, such as, for example, a dwelling.

It is still yet a further object of the present invention to provide foam spray apparatus and methods for applying insecticides to cracks and crevices or other spots where insects are found.

These and other objects are obtained in accordance with the present invention wherein there is provided a foam sprayer apparatus which is a manual compressed-air sprayer modified in accordance with the present invention. The sprayer apparatus comprises a container and a manual air pump carried by the container. The pump is operable to manually pump air into the container and create an air head therein. A discharge channel establishes fluid communication between the interior and exterior of the container, and has an inlet inside the container and an outlet outside the container. The discharge channel contains an air opening located inside the tank and above a level to which a supply of foaming composition is to be filled. The inlet of the channel is located below the level to which a supply of foaming composition is to be filled.

The foam sprayer apparatus further comprises a foaming chamber or other means for causing turbulence in a fluid received from the discharge channel. The foaming chamber has an inlet and an outlet. The inlet is coupled to the discharge channel. A discharge valve controls the flow of fluid through the discharge channel and foaming chamber. When the valve is open, fluid flows from the discharge channel to the foaming chamber, and from the foaming chamber to a nozzle.

The nozzle is in fluid communication with the outlet of the foaming chamber. In the preferred embodiment, the nozzle is coupled to a spray wand, lance or probe to facilitate the application of foam. The nozzle functions to discharge, under pressure, foam received from the foaming chamber when the discharge valve is opened. The nozzle contains a multiplicity of holes or pores through which the foam is forced. These holes or pores establish a foam flow rate through the nozzle.

In operation, the manual air pump is first removed from the container, and a foaming composition is then poured into the container to a given fill level. Then, the pump is mounted back onto the container. With the discharge valve closed, an air head is created inside the container by manually pumping the air pump. When the discharge valve is opened, the air head forces the foaming composition through the discharge channel, and some of the air head is permitted to enter the air opening in the channel and mix with the foaming composition therein. The mixture of foaming composition and air in the discharge channel flows into the foaming chamber where it undergoes turbulence and is turned into a dense foam. The resulting foam flows from the foaming chamber and out through the nozzle.

In the preferred embodiment, a predetermined level is established in the container to which the foaming composition is to be filled, and the air opening contained in the discharge channel is located adjacent to and just above this predetermined level. Also, in the preferred embodiment, the discharge channel includes a dip tube situated substantially inside the container. The inlet of the dip tube is at or near the bottom of the container and the outlet of the dip tube is outside the container. The dip tube contains four air openings inside the container, located at the same point on the tube and equally spaced from each other around the perimeter of the tube. The discharge channel also includes a hose coupled to the outlet end of the dip tube. The other end of the hose is coupled to an inlet end of the foaming chamber. The discharge valve is located at the outlet end of the foaming chamber. The spray wand is coupled to the discharge valve, and the nozzle is coupled to the outlet end of the spray wand.

The foaming chamber contains at least one screen member which is disposed transversely to the direction of flow of foaming composition entering the chamber. This screen member may simply be a standard in-line poly screen filter normally used in some compressed-air sprayers. However, the foaming chamber may contain a plurality of layered or juxtaposed screen members disposed transversely to the direction of flow of foaming composition entering the chamber.

The nozzle may be made of sintered metal which contains a multiplicity of pores or passageways through which the foam is discharged. Alternatively, the nozzle could be constructed of a rolled-up sheet of metal containing many small holes.

Methods of applying foam are also contemplated by the present invention. One such method concerns the treatment of insects using an insecticidal foaming composition and a manual compressed-air sprayer which has been modified in accordance with the present invention, as described above. The method comprises the steps of: (1) filling the container to a level with a pesticidal foaming composition; (2) manually pumping air into the container, using the manual pump, to create an air head therein; (3) opening the valve to permit the air head to push the foaming composition into the discharge channel, to permit some of the air head to enter the air opening in the discharge channel and mix with the foaming composition therein, to permit the mixture of foaming composition and air to flow into the foaming chamber where it undergoes turbulence and is turned into an insecticidal foam, and to permit the foam to flow from the foaming chamber and out through the nozzle; and (4) applying the insecticidal foam to a target location for treatment of insects by manually directing the nozzle.

Another method concerns the treatment of fire ants in the fire ant mound. This method includes the use of a spray wand or probe which is coupled to a source of insecticidal foam. A nozzle is coupled to the discharge end of the wand. The method comprises the steps of: (1) inserting the nozzle end of the wand into the fire ant mound such that the nozzle is approximately at the center of the mound; and (2) injecting insecticidal foam into the mound by causing a flow of insecticidal foam from the foam source, to and through the wand, and out through the nozzle.

In the preferred embodiment, this method includes the step of depositing a bead of insecticidal foam on the outside surface of the mound at the point where the wand has been inserted or at the point selected for insertion. The preferred method may also include the step of depositing a barrier of insecticidal foam around the perimeter of the fire ant mound to contain any ants attempting to escape. An alternative step may include depositing a layer of insecticidal foam over the entire outside surface of the mound before or after inserting the wand into the mound. The preferred source of insecticidal foam is a manual compressed-air sprayer modified in accordance with the present invention.

It is a further method of the present invention to apply an insecticide barrier along a target surface, such as a dwelling, using a manual compressed-air sprayer constructed in accordance with the present invention. This method includes the use of an insecticide that leaves behind an effective killing residue after the foam has dissipated.

It is yet a further method of the present invention to apply an insecticidal foam to cracks, crevices and other places where insects are found, using a manual compressed-air sprayer modified in accordance with the present invention.

BRIEF DESCRIPTION OF THE DRAWING

Further objects of the present invention will become apparent from the following description of the preferred embodiments with reference to the accompanying drawing, in which:

FIG. 1 is a cross sectional view of a manual compressed-air sprayer apparatus embodying the teachings of the present invention;

FIG. 1A is a cross sectional view of an alternative embodiment of a handle assembly for the sprayer apparatus of FIG. 1, which includes a foaming chamber and discharge valve.

FIG. 2 is an enlarged, exploded view of the handle assembly of the sprayer apparatus of FIG. 1, showing a number of screen disc members to be inserted into the foaming chamber;

FIG. 2A is an enlarged side elevation view of an in-line filter which is intended to replace the screen disc members inside the foaming chamber;

FIG. 3 is an enlarged cross sectional view of a sintered metal nozzle for the sprayer apparatus of FIG. 1;

FIG. 4 is an enlarged perspective view of a screen disc member used in the foaming chamber of the spray apparatus of FIG. 1;

FIG. 5 is an enlarged perspective view of a segment of a dip tube which is employed in the container of the spray apparatus of FIG. 1, showing an arrangement of air inlet opening in accordance with the present invention;

DESCRIPTION OF THE PREFERRED EMBODIMENTS

Figure 6:
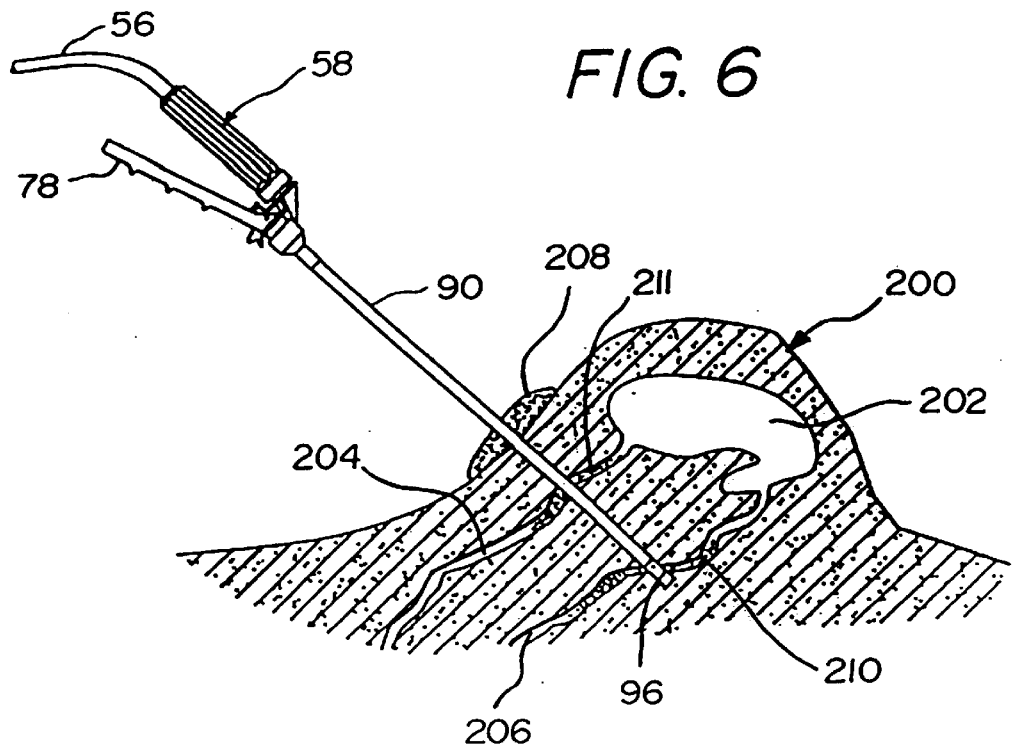
FIG. 6 is a diagrammatic view of a method of treating fire ants in the fire ant mound in accordance with the present invention.

Referring to FIG. 1 of the drawing, there is shown a foam sprayer apparatus 10 constructed in accordance with the present invention. Sprayer 10 is a manual compressed-air sprayer that has been modified in accordance with the teachings of the present invention. Sprayer 10 may be constructed from a commercially available compressed-air sprayer, such as the Smith Professional Sprayer™, Model DP2 (2 gallon capacity), manufactured by D. B Smith & Co., Inc., New York Mills, N.Y.

As shown in FIG. 1, sprayer 10 includes a container 12 which may be constructed of a chemically resistant material such as polyethylene or stainless steel. Sprayer 10 is intended primarily for applying chemical compositions such as insecticides, and thus container 12 must be inert to such compositions.

Sprayer 10 also includes a pump assembly 14 which is carried by container 12. Pump assembly 14 includes a pump cylinder 16 and a piston 18. Piston 18 is configured and dimensioned to slidably engage the interior surface of the cylindrical wall of cylinder 16. Piston assembly 18 is threaded onto a threaded end of a piston rod 20. The other end of piston rod 20 is formed in the shape of a handle frame 21 which includes a pump handle 22. Frame 21 terminates at a locking end 23. As understood from FIG. 1, the completed assembly of rod 20 and piston 18 is designed for reciprocating motion, between an extreme down position and an extreme up position. Locking end 23 functions to lock piston 18 in the extreme down position by engaging a notch contained in the cap (cap 36) of the container (notch is not shown).

With further reference to FIG. 1, the end wall of pump cylinder 16 contains four exhaust ports 24 (two of which are shown), and a check or umbrella valve 26. Piston 18 contains four, equally spaced, equalization ports 28 (two of which are shown), and a check or umbrella valve 30. Check valves 26 and 30 function, during the upward and downward strokes of piston 18, to cause air to be pumped from outside container 12 to the interior of container 12. Thus, air communication is established between the exterior and the interior of container 12, via pump assembly 14.

As understood from FIG. 1, piston 18 is actuated manually by grasping handle 22 and moving handle 22 in an upward and downward direction. On the upward stroke, a partial vacuum is created below piston 18, causing check valve 30 to open and allow air to flow through ports 28 and into the volume of cylinder 16 below piston 18. On the downward stroke of handle 22, the air is pressurized in the volume below piston 18 until valve 26 is forced open. Upon the opening of valve 26, the pressurized air passes through exhaust ports 24 and into container 12, creating an air head inside container 12.

The top portion of cylinder 16 contains buttress or sealing threads 32 which engage corresponding threads at the neck region of container 12, as shown in FIG. 1. This threaded engagement establishes an air tight seal for container 12. The upper-most end of cylinder 16 contains a pair of resilient locking tabs 34 which are in a snaplock engagement with a pump cap 36 (See FIG. 1). An outer annular rim 37 tightly fits over a rim 38 of container 12. A spring 40, slipped around pump rod 20, rests on cap 36, as shown in FIG. 1. Spring 40 acts as a shock absorber against a downward stroke of handle frame 21.

With further reference to FIG. 1, a discharge channel 42 establishes fluid communication between the interior and exterior of container 12. Discharge channel 42 comprises a dip tube 44 which contains an inlet end 46 and an outlet end 48. Tube 44 also contains four air inlet openings 50 which are located at the same point along dip tube 44 and equally spaced around the perimeter thereof (See also FIG. 5). Air openings 50 are situated just above a fill line or level 52 when dip tube 44 is installed in container 12. As shown in FIG. 1, when dip tube 44 is in place, inlet 46 is located below fill line 52. Fill line 52 is a level to which a supply of foaming composition 53 is to be filled inside container 12. In the preferred embodiment, air holes 50 are situated adjacent to fill line 52 to achieve optimum foaming performance, as will be explained hereinbelow.

As shown in FIG. 1, container 12 has an outlet ferrule 54, configured as a hose fitting. Dip tube 44 is slipped through ferrule 54 during assembly of apparatus 10, and is carried by ferrule 54 because of a flange 49 at the outlet end 48 of tube 44. Discharge channel 42 also includes a chemically resistant, reinforced hose 56. One end of hose 56 is tightly fitted onto ferrule 54. A hose clamp (not shown) is used to clamp the end of hose 56 to ferrule 54. The other end of hose 56 is coupled to a handle assembly 58.

As shown in FIG. 1, handle assembly 58 comprises a chamber housing 60 which in turn contains a cylindrical foaming chamber 62. An inlet end 64 of chamber housing 60 is configured as a hose fitting 65 for receiving the other end of hose 56. A hose clamp (not shown) is used to clamp the end of hose 56 to fitting 65. The outlet end of chamber 60 is threaded onto a threaded fitting 68 (See also FIG. 2). The diameter of chamber 62 is larger than the inside diameter of hose 56. Thus, chamber 62 allows for some expansion of the foaming composition as it flows from discharge channel 42 into chamber 62. The transition from a smaller diameter to a larger diameter also causes some turbulence in the composition as it enters chamber 62. The function of chamber 62 is to create turbulence in the composition and transform it into a useful foam.

To enhance the turbulence in chamber 62, a number of screens 70 may be inserted in juxtaposed fashion in chamber 62 (See FIGS. 1 and 2). The number of screens is not critical. However, in the example shown, ten polyethylene screens are employed. An enlarged perspective view of one of the screens is shown in FIG. 4. Note from FIG. 1 that the screens do not occupy the entire volume of chamber 62. A sub-chamber or space chamber 63 is present. The combination of multiple screens 70 and space chamber 63 will create a dense foam (10:1 ratio of foam to liquid composition) without much pressure drop at the nozzle. Thus, the foaming means of apparatus 10 does not substantially diminish the flow rate and pressure at the nozzle, as would occur in many prior art devices (such as those using a flow restrictor).

Other means for enhancing the turbulence in chamber 62 may include glass beads, steel wool, plastic wool, steel or plastic screen, steel or plastic shot, filter media, sponge or foam rubber.

In an alternative embodiment, and one that is currently preferred, a screen filter 170 is employed in place of discs 70. This embodiment is shown in FIG. 1A. An enlarged elevation view of filter 170 is shown in FIG. 2A. Filter 170 may be constructed of any suitable material. One such material is polyethylene.

With reference to FIGS. 1 and 2, handle assembly 58 further comprises a branch member 72 containing a branch channel 74. Channel 74 establishes fluid communication between chamber 62 and a discharge valve 76. Valve 76 is actuated between closed and open positions by operating a trigger handle 78 between respective closed and open positions. Trigger handle 78 can be locked in the open position by means of a trigger lock 80. Valve 76 comprises a brass check head 82 having an elongated stem 83. In the closed position, check head 82 is seated tightly against a nylon valve seat 84. A compression spring 86 is slipped around stem 83 of check head 82, and functions to urge check head 82 against seat 84 (See FIG. 1). Handle 78 is linked to stem 83 by a transverse pin 88 (See also FIG. 2). As handle 78 is manually depressed from its closed position to an open position, check head 82 is pulled back against the force of spring 86 to effect the open position of valve 76. As shown in FIG. 1, valve seat 84 contains a centrally disposed discharge port 85. In the open position of valve 76, fluid is permitted to flow from chamber 62, through branch channel 74, through discharge valve 76, and out through discharge port 85.

An alternative embodiment of handle assembly 58 is shown in FIG. 1A. As shown in FIG. 1A, a handle assembly 158 comprises a chamber housing 160. Housing 160 contains a tubular foaming chamber 162. Contained within chamber 162 is an elongated screen filter 170 (See also FIG. 2A). Handle assembly 158 is otherwise identical to handle assembly 58, including an identical discharge valve 176 and a trigger handle 178.

A side elevation view of screen filter 170 is shown in FIG. 2A. Filter 170 is substantially cylindrical in shape, but has a slight taper towards a closed end 180. Disposed between ridged cross members 171 are polyethylene screen windows 169. The other end 181 of filter 170 is open and contains a resilient engaging flange 182. The function of flange 182 is to establish a compression fit with the interior wall of fitting 168 of handle assembly 158 (See FIG. 1A).

Referring back to FIG. 1, there is shown a spray wand, lance or probe 90 containing an axial passageway therethrough. Probe 90 has an inlet end 92 coupled to handle assembly 58 at the discharge port of valve 76. Probe 90 is essentially a ridged tube made of brass, stainless steel or polyethylene. Probe 90 includes an outlet or distal end 94 to which is coupled a foaming nozzle 96. Nozzle 96 is fixedly secured to end 94. In the preferred embodiment, nozzle 96 is constructed of a cylindrical piece of sintered metal containing a multiplicity of pores 97 or passageways.

An enlarged cross-sectional view of nozzle 96 is shown in FIG. 3. Pores 97 present a maze of meandering channels between a nozzle cavity 98 and a discharge surface 99. Nozzle 96 establishes a back pressure in cavity 98 which is sufficient to push the foam through pores 97 with enough force so that the foam can be propelled through tunnels and cavities, if necessary for a particular application. In addition, pores 97 function to eliminate squirting of foam through the nozzle by restricting the velocity of the foam. A preferred flow rate of foam through nozzle 96 is 2 ½ to 3 gallons of foam per minute.

In an alternative embodiment, nozzle 96 may be constructed of sheet metal containing a multiplicity of holes approximately two thousandths of an inch in diameter (0.002 inches). The perforated sheet metal is then formed into a cylindrical roll, and one end is spot welded or pinched to complete the manufacture.

FIG. 4 shows an enlarged perspective view of one of the screen discs. Disc 70 contains a screen face 69 and three beads 71. Disc 70 is constructed of polyethylene plastic. While not necessary, beads 71 function as spacers between juxtaposed screen discs, as understood from FIG. 2.

FIG. 5 illustrates an enlarged perspective view of a segment of dip tube 44. This illustrated segment contains the four air inlet openings 50 in dip tube 44. As shown, openings 50 are equally spaced around the perimeter of dip tube 44 (i.e., spaced 90°). The preferred diameter for openings 50 is twenty thousandths of an inch (0.020 inches). Air openings 50 admit a portion of the air head, generated in container 12, into tube 44 where it mixes with the foaming composition being drawn up through tube 44. It has been determined empirically that the optimum location for air openings 50 is close to fill level 52 for foaming composition 53. This location is optimum because it maximizes the length over which the mixed air and foaming composition travels before reaching foaming chamber 62. It has been found that by increasing this length for the air/composition mixture, a more consistent, denser foam is produced in foaming chamber 62. In addition, the expansion ratio of the foam (i.e., ratio of foam to liquid) is increased.

In the operation of apparatus 10, pump assembly 14 and pump cap 36 are removed from container 12. A foaming composition, including a foaming agent and an application liquid (such as, e.g., an insecticide solution or simply water) is poured into container 12 to predetermined fill level 52. In the embodiment shown in FIG. 1, fill level 52 is set at approximately fifty percent (50%) of the fluid capacity of container 12 to insure an adequate operating pressure (i.e., air head). After the filling operation, pump assembly 14 and cap 36 are mounted back onto container 12, to begin the manual pumping operation. With valve 76 in the closed position (handle 78 is not depressed), pump assembly 14 is manually actuated to pump air into container 12 and create an air head above the surface of foaming composition 53. For preferred operation, an air head of between 20 and 30 pounds per square inch (psi) should be created inside container 12. The embodiment shown in FIG. 1 represents a two gallon unit, holding about one gallon of liquid foaming composition. The number of pump strokes required to produce the preferred air head is between about 30 and 50. The optimum pressure head for the embodiment of FIG. 1 is 30 psi.

Once an air head is created in container 12, a portion of the air head is admitted through openings 50. At the same time, the air head pushes down on composition 53, causing air to enter inlet end 46 and travel up through dip tube 44. As the foaming composition reaches air openings 50 the air entering these holes mixes with the foaming composition, and this mixture travels up and out through dip tube 44, and into hose 56. The air head provides sufficient pressure to force the air/foaming composition mixture through tube 56 and into foaming chamber 62. As this mixture enters foaming chamber 62, it undergoes a significant amount of turbulence as it passes through screen discs 70 and accumulates in the expanded volume of space chamber 63. As a result of this turbulence, the mixture is converted into a dense foam. Upon depression of handle 78, discharge valve 76 is pulled open, permitting a flow of foam from chamber 62, through channel 74, into valve 76, through discharge port 85, through probe 90, and into nozzle cavity 98. The foam is then forced under pressure through pores 97 of nozzle 96 and expelled out from the surface of nozzle 96.

Heretofore the term "foaming composition" has been used to describe a solution containing a foaming agent and an application liquid (such as an insecticide solution). In its simplest form, foaming composition 53 may consist of simply a foam agent and water. In another example, foaming composition 53 may contain a foaming agent, a cleaning agent, and water. The components of foaming composition 53 depends on the application intended for the foam to be produced by apparatus 10.

One particular application for apparatus 10 is the treatment of fire ants in ant hill mound. One foaming composition that may be used for treating fire ants comprises: (1) one ounce of an insecticide concentrate which contains 1.1% w/w of Rotenone, 2.2% w/w of other cube extractives, 0.8% w/w of Pyrethrins, and 95.9% of inert ingredients; (2) three ounces of a foaming agent called PCO Foam™ (a/k/a FM-1), manufactured by Kalo, Inc., Overland Park, Kans., which consists of sodium lauryl ether sulfate, isopropanol alcohol, linear alcohol, polyether polyol, dihexyl sodium sulfosuccinate, water and a colorant; and (3) one gallon of water, preferably soft water. The insecticides used that are botanical and do not leave a long lasting residue. Thus, this composition is environmentally friendly, which is desirable for some house and garden applications.

Other foaming compositions are effective for treating fire ants. For example, the most effective composition tested contains an insecticide called Permetherin. The composition comprises: (1) one ounce of Permethrin®; (2) three ounces of foaming agent (e.g., PCO Foam™); and (3) one gallon of water. Another composition uses Rotenone powder. This composition comprises: (1) three ounces of Rotenone powder; (2) three ounces of a foaming agent (e.g., PCO Foam™); and (3) one gallon of water.

The foaming compositions described above produce a dense foam when used in apparatus 10 of FIG. 1. Foaming ratios of between 8:1 and 15:1 are achieved in apparatus 10, using the above compositions. The preferred range of foaming ratios is between 10:1 and 15:1. For the application of treating fire ants, it is desirable to have a foaming ratio of less than 20:1. The foaming ratio is defined as the ratio of—the volume of foam produced to the volume of liquid used to produce the foam. If one gallon of liquid produces 15 gallons of foam, the foaming ratio is 15:1. The foam produced from these compositions has a life of approximately one to two hours depending on atmospheric conditions.

Methods of treating fire ants employing foam sprayer apparatus 10 will now be described with reference to FIGS. 6–9. In accordance with the operating procedures described above, foam sprayer apparatus 10 is prepared to deliver pressurized insecticidal foam through nozzle 96. Before releasing the foam through nozzle 96 (by depressing handle 78), nozzle 96 and the distal end of probe 90 is inserted into the fire ant mound until nozzle 96 is about at the center of the mound, as shown in FIG. 6. At this point, handle 78 is depressed to open discharge valve 76 and cause pressurized foam to be injected into the mound. In FIG. 6, an ant hill mound 200 contains a chamber 202, and tunnels 204 and 206. As understood from FIG. 6, nozzle 96 is inserted into mound 200 to a point, estimated to be the center of mound 200, where it can inject a deposit of foam 210 in tunnel 206. As probe 90 is withdrawn from mound 200, the operator may maintain handle 78 in the depressed position. Thus, when nozzle 96 traverses tunnel 204, a deposit of foam 211 is injected into tunnel 204 (See FIG. 6).

Tests have demonstrated that the foam injected into the tunnels of a mound, travels a length of about six (6) inches from the point of discharge at nozzle 96. Theoretically then, the effective area of treatment, for one probe and one application, is 12 inches in diameter. The typical fire ant mound is 12 inches in diameter.

Fire ants are prone to attack any invaders of the mound. Once probe 90 is inserted into the mound, fire ants are likely to attack and crawl up probe 90. To prevent such an occurrence, a bead of insecticidal foam 208 is deposited on the surface of mound 200, at the point of insertion of probe 90 (See FIG. 6). Bead of foam 208 may be deposited either before or after insertion of probe 90 into mound 200. It is the preferred practice to deposit bead 208 before initially inserting the probe into the mound.

Figure 7:
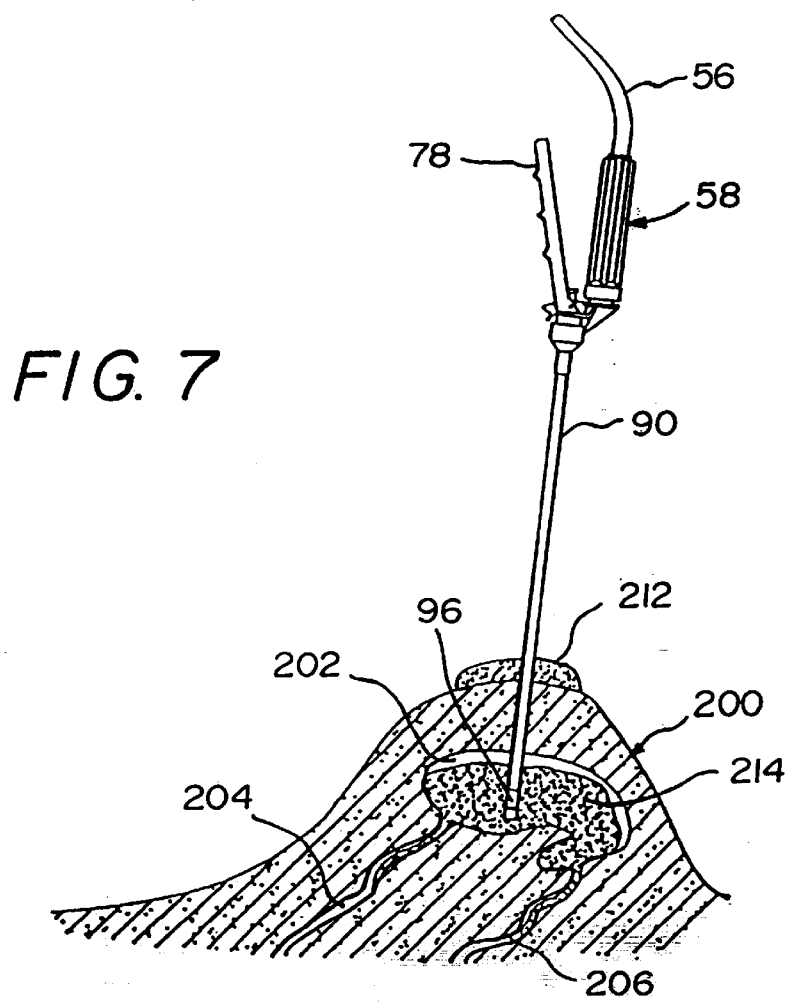
FIG. 7 is a diagrammatic view of a variant of the method of FIG. 6.

FIG. 7 illustrates essentially the same method described with reference to FIG. 6, except that probe 90 is inserted down through the top of mound 200. As shown in FIG. 7, a bead of insecticidal foam 212 is initially deposited at the top of mound 200. Probe 90 is then inserted through foam bead 212 and into mound 200 to about the center point. Pressurized insecticidal foam 214 is then deposited inside central cavity 202 by depressing handle 78 to cause a flow of foam through probe 90 and out of nozzle 96.

Figure 8:
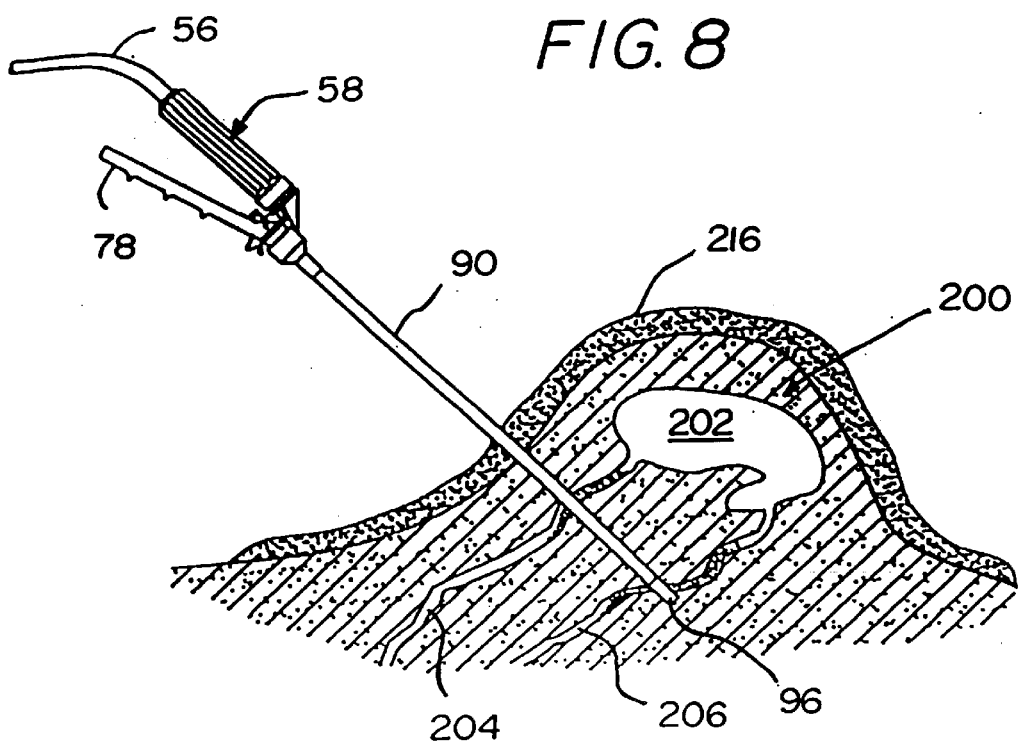
FIG. 8 is a diagrammatic view of another variant of the method of FIG. 6.

Referring now to FIG. 8, another method of treating fire ants in the mound is illustrated. Like the methods described with reference to FIGS. 6 and 7, this method is performed by using foam sprayer apparatus 10. In this method, a blanket or layer of insecticidal foam 216 is initially deposited over the entire surface of mound 200. Probe 90 is then inserted through blanket of foam 216, and foam is injected into tunnels 204 and 206 in the same manner as described above with reference to FIG. 6.

Figure 9:
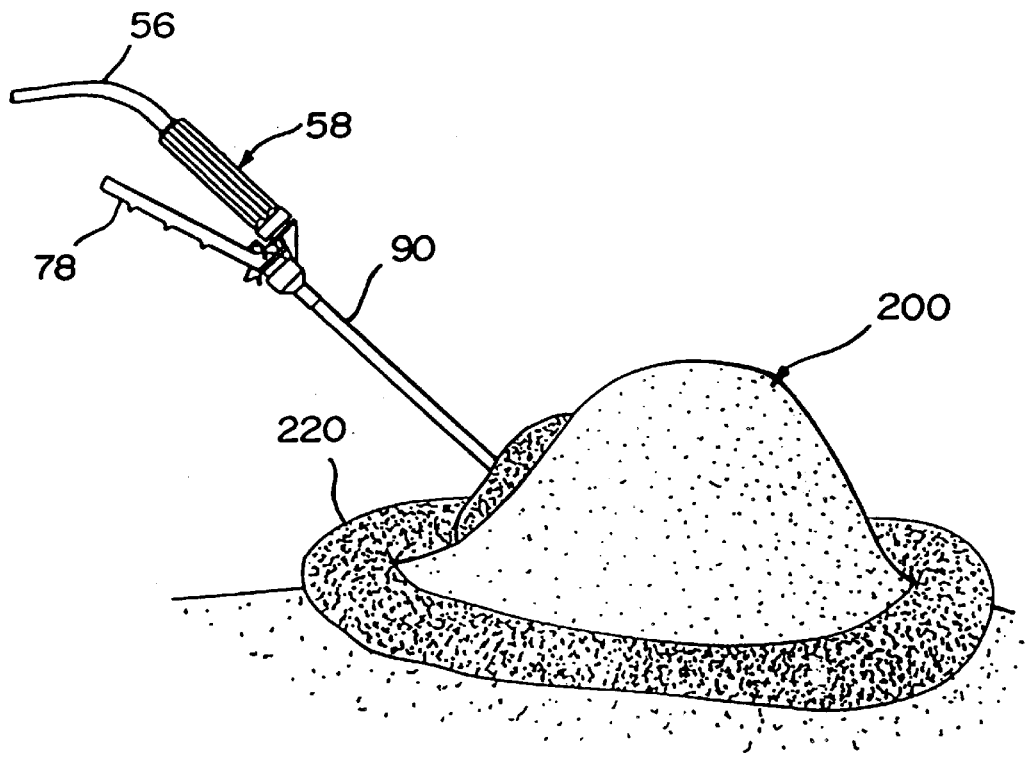
FIG. 9 is a diagrammatic view of a further variant of the method of FIG. 6.

A further method of treating fire ants is illustrated in FIG. 9. This method is identical to the method described with reference to FIG. 6, except that upon withdrawing probe 90 from mound 200, a barrier of insecticidal foam 220 is deposited around the perimeter of mound 200, using apparatus 10. Barrier 220 entraps the fire ants, preventing them from attaching the operator or getting away.

In all of the above-mentioned methods of treating fire ants, the step of inserting probe 90 into mound 200 may be repeated one or more times depending on what is necessary to destroy the ant colony in mound 200. Probe 90 is withdrawn from mound 200 after an initial injection step, and then reinserted back into the mound. Then the step of injecting insecticidal foam into mound 200 is repeated.

Apparatus 10 has been field tested on fire ant mounds to determine its effectiveness. When using the Rotenone/Pyrethrin based foaming composition, with one application, about 42% of the mounds treated were eliminated, and about 85%–95% of the ants from the mounds treated were killed. When using the Rotenone powder based foaming composition, with one application, about 10% of the mounds treated were eliminated, and about 75%–85% of the ants from the mounds treated were killed. When using the Permethrin® based foaming composition, with one application, about 80% of the mounds treated were eliminated, and about 94%–96% of the ants from the mounds treated were killed. These tests demonstrated that the fire ant queens, larvae, eggs and worker ants can be destroyed with the apparatus and methods of the present invention. The results of these tests also suggest that a residual insecticide used in the foaming composition may be best because forager ants, not in the mound during treatment, return later and are killed by the residue.

The above-described methods of treating fire ants have at least three major advantages over previous methods. First, the insecticidal foam will follow the path of least resistance and flow through tunnels where the ants are located, allowing more insecticide to come in contact with the fire ants, and not be absorbed by the soil. Second, the foam is perceived by the fire ant as an invader. The fire ant will attack the foam because of its aggressive nature. Thus, ants that were not in the direct path of the foam, will be drawn to it and exposed to the insecticide. Third, the foam immediately isolates and contains the ant colony.

The preferred nozzle for treating fire ants is the sintered metal nozzle, described above with reference to FIGS. 1 and 3. This nozzle is strong and can be pushed into the ground. The fine pores contained in the sintered metal allow the foam to flow out, but prevent the soil from plugging the nozzle when it is inserted into the mound.

Figure 10:
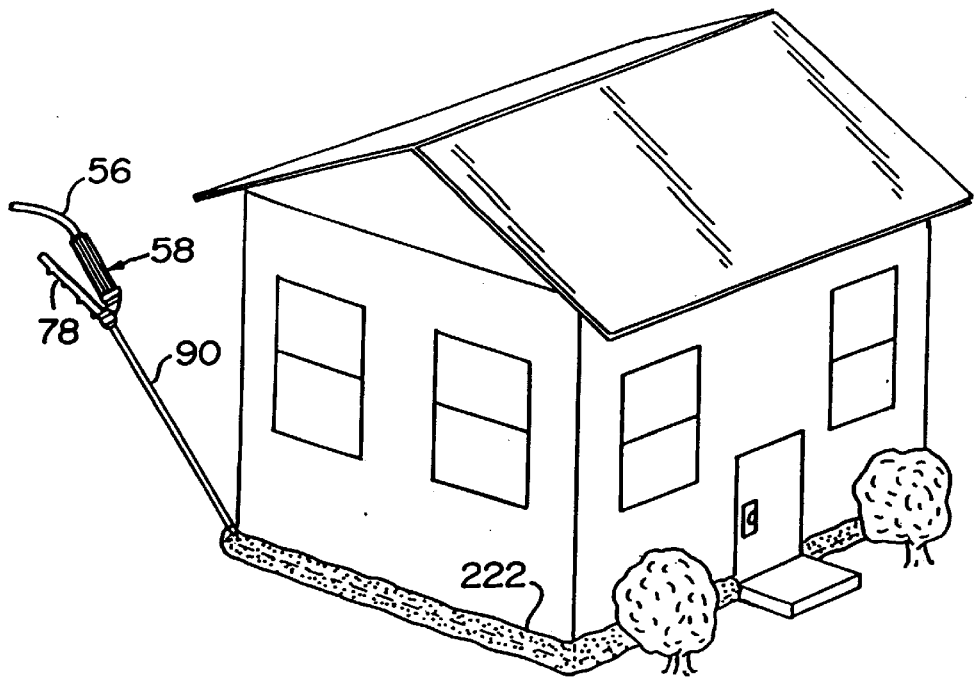
FIG. 10 is a diagrammatic view of a method of applying an insecticide barrier around a dwelling, using spray apparatus of the present invention.

Another method of the present invention is illustrated in FIG. 10. In FIG. 10, foam sprayer apparatus 10 of the present invention is employed as a barrier sprayer. In this method, apparatus 10 is used to apply an insecticidal foam that contains a residual insecticide. The foam is applied around the perimeter of a structure, such as a dwelling, to create an insecticidal barrier 222 for crawling insects, as shown in FIG. 10. This barrier kills or repels insects that crawl near the barrier. The use of a foam insecticide to create a barrier has the advantage that the foam provides a visual indicator for the operator, as he or she lays down the barrier. The operator can then be sure that a continuous barrier is laid down around the structure. In addition, there is the advantage that the foam prevents the insecticide from being blown away during application. It is thus a more efficient method of applying a barrier than spraying a liquid insecticide and eliminates any airborne particles.

In the method of applying an insecticidal barrier, sprayer apparatus 10 is prepared to discharge foam in the same manner as described above with reference to FIG. 1. The preferred target surface for the barrier is a portion of the foundation wall of the structure and a portion of the adjacent ground surrounding the wall, as shown in FIG. 10. This target surface may be as narrow as about 1 ½ to 2 inches wide.

The preferred foaming composition for the method of applying an insecticidal barrier is now described. The foaming composition comprises: (1) four ounces of Permethrin®; (2) three ounces of a foaming agent, such as PCO Foam®; and (3) a gallon of water. To be effective, the insecticide must leave an effective killing residue for a period of one to two weeks.

Figure 12:
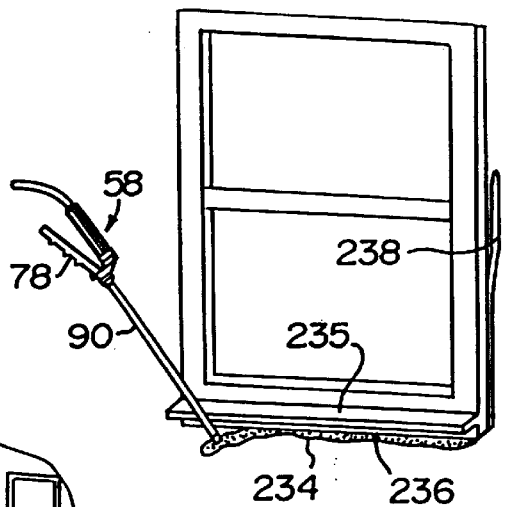
FIG. 12 is a diagrammatic view of a method of applying an insecticidal foam to cracks along a window of a dwelling, using apparatus of the present invention.
Figure 11:
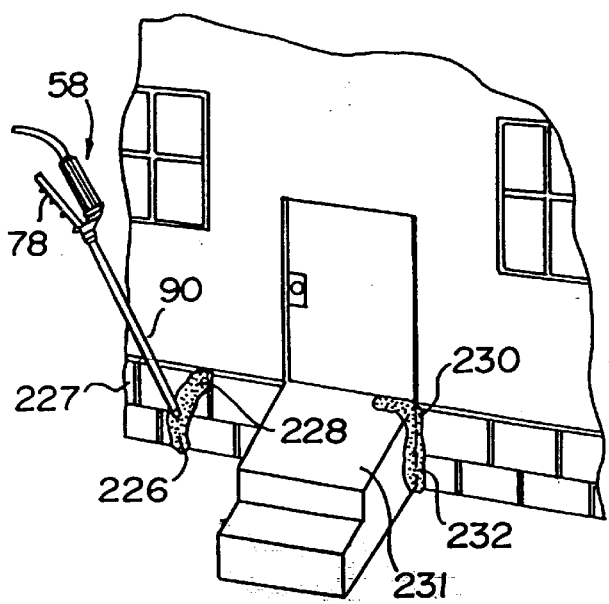
FIG. 11 is a diagrammatic view of a method of applying an insecticidal foam to cracks and crevices of a dwelling, using spray apparatus of the present invention.

Referring now to FIGS. 11 and 12, there is illustrated a further method of the present invention. FIGS. 11 and 12 illustrate a method of spot treating a specific target area with an insecticidal foam. The method employs foam sprayer apparatus 10 of the present invention. As shown in FIG. 11, probe 90 is manually directed to a crack 226 in a foundation 227 of a dwelling, and an insecticidal foam 228 is applied thereto. Also in FIG. 11, a crevice 230 is shown between a stoop 231 and foundation 227. A layer of insecticidal foam 230 has been deposited on this crevice using apparatus 10 of the present invention.

FIG. 12 further illustrates another example of spot treating a target area with an insecticidal foam. Probe 90 is applied to a crack 234 adjacent to a window sill 235. A layer of insecticidal foam 236 is applied to cover crack 234. A vertically disposed crack 238 is also shown adjacent to the window frame, and provides another target area for application of the insecticidal foam.

The preferred foaming composition for the method of spot treating a specific target area is now described. The foaming composition comprises: (1) four ounces of Permethrin®; (2) three ounces of a foaming agent, such as PCO Foam®; and (3) a gallon of water. To be effective, the insecticide must leave an effective killing residue for a period of two weeks.

While the preferred embodiments of the invention have been particularly described in the specification and illustrated in the drawings, it should be understood that the invention is not so limited. Many modifications, equivalents and adaptations of the invention will become apparent to those skilled in the art without departing from the spirit and scope of the invention, as defined in the appended claims.

What is claimed is:

1. A method of treating fire ants in a mound using a probe which contains a fluid passage therethrough and has an inlet end and a discharge end, wherein the inlet end of said probe is coupled to a source of insecticidal foam, the method comprising the steps of:

(a) depositing a bead of insecticidal foam on an outside surface of the mound at a point selected for inserting the probe;

inserting the discharge end of said probe through the bead and into the fire ant mound; and (c) injecting insecticidal foam into the mound by causing a flow of insecticidal foam from said foam source, to and through said probe, and out of the discharge end of said probe.

2. The method as recited in claim 1, wherein step (a) includes inserting the discharge end of said probe to approximately the center point of said mound.

3. The method as recited in claim 1, further comprising the steps of (a) withdrawing the discharge end of said probe from the mound;

(b) reinserting the discharge end of said probe into the mound; and (c) repeating step (b).

4. The method as recited in claim 1, further comprising the steps of (a) withdrawing the discharge end of said probe from the mound; and (b) depositing a barrier of insecticidal foam around the perimeter of the fire ant mound.

5. A method of treating fire ants in a mound using a probe which contains a fluid passage therethrough and has an inlet end and a discharge end, wherein the inlet end of said probe is coupled to a source of insecticidal foam, the method comprising the steps of:

(a) depositing a layer of insecticidal foam on an outside surface of the fire ant mound;

(b) inserting the discharge end of said probe through the layer and into the fire ant mound; and (c) injecting insecticidal foam into the fire ant mound by causing a flow of insecticidal foam from the foam source, to and through the probe, and out of the discharge end of the probe.

* * * * *